United States Patent [19]

Kato et al.

[11] Patent Number: 4,939,128
[45] Date of Patent: Jul. 3, 1990

[54] ESTER OF ASCORBIC ACID 2-PHOSPHATE AND PHARMACEUTICAL USE

[75] Inventors: Kaneyoshi Kato, Osaka; Norio Shimamoto, Hyogo, both of Japan

[73] Assignee: Takeda Chemical Industries, Ltd., Osaka, Japan

[21] Appl. No.: 333,234

[22] Filed: Apr. 5, 1989

[30] Foreign Application Priority Data

Apr. 25, 1988 [JP] Japan ................................. 63-101935

[51] Int. Cl.$^5$ ...................... A61K 31/665; C07F 9/09
[52] U.S. Cl. .................................... 514/82; 514/99; 514/100; 540/5; 546/23; 549/220; 549/222
[58] Field of Search .................. 549/220, 222; 546/23; 540/5; 514/82, 99, 100

[56] References Cited

U.S. PATENT DOCUMENTS 4,564,686 1/1986 Ogata .................................. 549/220

FOREIGN PATENT DOCUMENTS 0202589 11/1986 European Pat. Off. .
0236120 9/1987 European Pat. Off. .

OTHER PUBLICATIONS

Hiroaki Nomura et al., "Studies on L-Ascorbic Acid Derivatives The Ferric Chloride Reaction of L-Ascorbic Acid 3-Phosphate and its Application for the Colorimetric Determination", Chem. Pharm. Bull., vol. 19(2), (1971) pp. 335-340.

Primary Examiner—Richard L. Raymond
Attorney, Agent, or Firm—Wegner & Bretschneider

[57] ABSTRACT

The present invention relates to a compound of the formula:

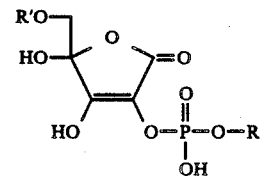

wherein $R^1$ is a hydrogen atom, carboxylic acid acyl or carbamoyl which may be substituted; R is an aliphatic hydrocarbon group which may be substituted or alicyclic hydrocarbon group which may be substituted, or a salt thereof.

The compound of the present invention has the effects to prevent and improve dysfunctions caused by oxygen free radicals, and can be used as preventive and therapeutic drugs against dysfunctions in the circulatory system.

12 Claims, No Drawings

ESTER OF ASCORBIC ACID 2-PHOSPHATE AND PHARMACEUTICAL USE

This invention relates to the phosphoric acid esters of ascorbic acid and the method for production thereof.

Diseases of heart, brain, kidney and liver which are encountered frequently in adults are mainly due to the lesions and death of cells and tissues caused by ischemia, the underlying disorder which interrupts energy supply because of hemostasis. For example, ischemic heart diseases, cerebral ischemic disorders, ischemic nephropathy, and ischemic ulcers of the digestive system have become the leading causes of death along with the increase of the morbidities in the advanced countries in the course of development of the highly civilized and aging society.

It has recently been clarified that active oxygen species and active organic radical species play important roles in the development of lesions in the ischemic tissues, i.e. in decrease and disturbance of cellular functions, and destruction and necrosis of cells [I. Fridovich, Annual Review of Pharmacology and Toxicology, 23, 239 (1983); J. M. McCord, The New England Journal of Medicine, 312, 159 (1985); K. P. Burton, J. M. McCord, and G. Ghai, American Journal of Physiology, 246, H776 (1984)].

Active oxygen species and active organic radical species present in organisms include superoxide ($O_2^-$), hydroxy radical (.OH), singlet oxygen ($^1O_2$), and peroxide radical (ROO.). Especially the relation between production of $O_2^-$ in organisms and the subsequent damages of cells or tissues by the active oxygen species is important. Excessive production of $O_2^-$ may be particularly important as the essential factor for tissue damages due to re-perfusion in the ischemic lesions or due to ischemia.

Superoxide dismutase which can eliminate $O_2^-$ efficiently and specifically is known to be effective for protection of the tissues and improvement of the damages due to ischemia-reperfusion or ischemia [D. N. Granger, G. Rutili and J. M. McCord, Gastroenterology, 81, 22 (1981)]. Compounds such as ascorbic acid, α-tocopherol, cystein, and reduced glutathione are effective in eliminating free radicals, and have been established to be able to prevent tissue damages which may be caused by free radicals under certain morbid conditions [I. Fridovich, Science, 201, 875 (1978)]. Also desferrioxamine having the iron-chelating activity is known to suppress tissue damages caused by active oxygen species.

The inventors have already clarified that 2-O-alkyl ethers of ascorbic acid are effective in treatment of dysfunction of the circulatory system because these compounds can eliminate active oxygen species [EP-A2-0 202 589 Specification].

For the treatment of acute diseases caused by active oxygen species, it is a pressing need to develop drugs with physicochemical properties that the drugs are water-soluble so that they can be administered parenterally in the form of injections.

As the result of the inventors, searches for such compounds, they found that some phosphoric acid esters of ascorbic acid have excellent characteristics, and have completed this invention.

This invention relates to a compound represented by the formula:

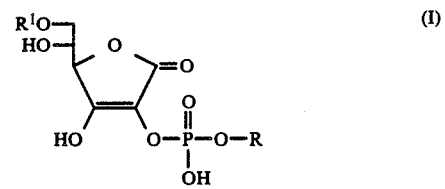

wherein $R^1$ as a hydrogen atom, carboxylic acid acyl or carbamoyl which may be substituted, R is an aliphatic hydrocarbon group which may be substituted or alicyclic hydrocarbon group which may be substituted, or a salt thereof, and the method for production of the compound or the salt thereof described above, characterized in that a compound represented by the formula:

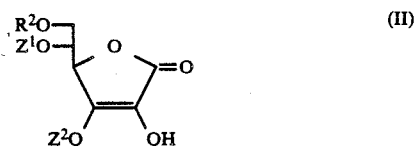

wherein $R^2$ is a hydroxyl-protective group, carboxylic acid acyl, or carbamoyl which may be substituted, $Z^1$ and $Z^2$ are independently hydrogen atoms or hydroxyl-protective groups, and a compound represented by the formula:

wherein R is an aliphatic hydrocarbon group which may be substituted, or alicyclic hydrocarbon group which may be substituted, and X is a halogen atom are allowed to react, followed by hydrolysis.

In the formula (I) above, the aliphatic hydrocarbon groups represented by R which may be substituted include non-cyclic hydrocarbon groups having 1 to 30 carbon atoms each, which may have 1 to 4 isolated or conjugate double bonds or triple bonds, that is, they may be alkyl, alkenyl or alkynyl. The hydrocarbon groups may be of straight chain or branched, the double bond in the alkenyls may be cis- or trans-form.

The aliphatic hydrocarbon groups, particularly alkyls, have desirably 1 to 22 carbon atoms each, more desirably 9 to 22 carbon atoms, and especially desirably 14 to 22 carbon atoms.

Such hydrocarbon groups are exemplified by methyl, ethyl, propyl, isopropyl, butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, and docosyl.

The number of methylene groups in the straight chain or branched alkyls which are substituted is desirably 1 to 21 each.

The alkenyls have desirably 5 to 24 carbon atoms each, and are exemplified by citronellyl, oleyl, linolyl, linoleyl, elaidyl, and erucanyl.

The substituents in the aliphatic hydrocarbon groups described above include hydroxyl groups which may be substituted, amino groups which may be substituted, carboxyl groups which may be substituted, aminocarbonyl groups which may be substituted, cycloalkyl groups which may be substituted, aryl groups which may be substituted, quinonyl groups which may be substituted, and chroman-2-yl groups which may be substituted.

Among the substituents in the aliphatic hydrocarbon groups, the hydroxyl groups substituted with alkyls having 1 to 20 carbon atoms each, phenyls which may be substituted with 1 to 3 halogen atoms (fluorine, chlorine, bromine, iodine atoms, etc.), $C_{1-3}$alkoxys, or $C_{1-3}$alkyls each, quinonyls which may be substituted with 1 to 3 $C_{1-3}$alkoxys or/and $C_{1-3}$alkyls (e.g. 2,3-dimethoxy-5-methyl-1,4-benzoquinon-6-yl), and chroman-2-yls which may be substituted with $C_{1-3}$alkyls, $C_{1-3}$alkoxys, hydroxyls, or phenyls (e.g. 2,5,7,8-tetramethyl-6-hydroxychroman-2-yl) are particularly desirable.

The alicyclic hydrocarbon groups represented by R which may be substituted include monocyclic hydrocarbon groups having 3 to 7 carbon atoms each (e.g. cyclopropyl, cyclobutyl, cyclohexyl, cyclopentyl), and condensed polycyclic hydrocarbon groups which are formed by condensation of two to five 3-6-membered rings (e.g. tetrahydroindanyl, tetrahydrotetranyl, cholestanyl, aldostanyl, pregnyl, ergostanyl). These alicyclic hydrocarbon groups may have 1 to 5 isolated or conjugate double bonds or triple bonds and may have 1 to 5 substituents such as 1 to 3 $C_{1-3}$alkoxys, $C_{1-3}$alkoxycarbonyls, hydroxyls, halogen atoms, straight chain or branched $C_{1-10}$alkyls, alkenyls or alkynyls (methyl, ethyl, propyl, isopropyl, vinyl, ethynyl, etc.).

The carboxylic acid acyls represented by $R^1$ and $R^2$ in the formulas described above include the acyls derived from carboxylic acids such as straight chain or branched fatty acids having 1 to 22 carbon atoms each, benzoic acid which may be substituted, phenylacetic acid which may be substituted, and dicarboxylic acids.

The said fatty acids include $C_{1-20}$ fatty acids such as formic acid, acetic acid, propionic acid, valeric acid, butyric acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid (stearic acid), nonadecanoic acid, eicosanoic acid, and isopropionic acid. The substituents in the said benzoic acid which may be substituted include $C_{1-3}$alkyls, $C_{1-3}$alkoxys, methylenedioxy, and halogens. The substituents in the said phenylacetic acid which may be substituted include $C_{1-3}$alkyls, $C_{1-3}$alkoxys, methylenedioxy, and halogens.

The acyls derived from dicarboxylic acids include those from $C_{1-3}$alkylmonoesters. The said dicarboxylic acids include malonic acid, succinic acid, glutaric acid, and adipic acid.

The substituents in the carbamoyl represented by $R^1$ and $R^2$ include $C_{1-20}$alkyls and monophenyls which may be mono- or di-substituted to the said $C_{1-20}$alkyls are exemplified by methyl, ethyl, propyl, isopropyl, butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, and docosyl.

When the compound (I) can form salts, the pharmaceutically acceptable salts may be used. The salts include salts of alkali metals such as sodium and potassium, salts of alkali earth metals such as calcium and magnesium, and ammonium salts.

The hydroxyl-protective groups represented by $R^2$, $Z^1$, and $Z^2$ in the compound (II) may be independently $C_{1-3}$-alkoxy-$C_{1-3}$alkyls (e.g. methoxymethyl, ethoxymethyl), and the hydroxyl-protective groups represented by $R^2$ and $Z^1$ may form ketals such as isopropylidene and cyclohexylidene or acetals such as benzylidene.

The halogen atoms represented by X in the compound (III) include chlorine and bromine atoms.

As described above, the compound (I) can be produced by the reaction of the compound (II) with the compound (III) followed by hydrolysis.

The reaction of the compound (II) with the compound (III) is carried out in a solvent such as aromatic hydrocarbons (e.g. benzene, toluene), ethers (e.g. diethyl ether, diisopropyl ether, dioxane, tetrahydrofuran), esters (e.g. ethyl acetate), halogenated hydrocarbons (e.g. methylene chloride, chloroform), dimethylformamide, or the mixtures thereof, at a temperature ranging from about $-10°$ to $50°$ C., for about 1 to 10 hours. The molar ratio of the compound (III) is usually 1.0 to 1.5 relative to the compound (II).

Hydrolysis in the production process described above is carried out in the presence of an acid catalyst such as hydrochloric acid, sulfuric acid, phosphoric acid, acetic acid, p-toluenesulfonic acid, methanesulfonic acid, and camphorsulfonic acid, in a mixed solvent composed of water and methanol, ethanol, dioxane, tetrahydrofuran, or 1,2-dimethoxyethane, at a temperature ranging from about $10°$ to $80°$ C., and the reaction completes in about 1 to 2 hours.

By this reaction the unnecessary hydroxyl-protective groups $R^2$, $Z^1$ and $Z^2$ and the residual halogen X are eliminated all together.

In the following the method for production of the compound (I) is explained in detail.

When ascorbic acid is used as the starting compound, ascorbic acid is first converted into acetals or ketals. The reaction is carried out by allowing ascorbic acid to react with a ketone or an aldehyde such as acetone, benzaldehyde, and cyclohexanone. The reaction is carried out without any solvent or in a solvent such as tetrahydrofuran, chloroform, diethyl ether, dichloromethane, and dichloroethane. The reaction is carried out at a temperature ranging from room temperature to $60°$ C. in the presence of an acidic catalyst. The catalysts include acetyl chloride, sulfuric acid, p-toluenesulfonic acid, and camphorsulfonic acid. The reaction time ranges from 1 to 24 hours.

The acetal or ketal derivatives of ascorbic acid thus obtained can immediately be used without any further treatment for production of the compound (I) by esterification with phosphoric acid at the hydroxyl group of the 2-position, but the hydroxyl group of the 3-position may be protected before the derivatives are subjected to the esterification. Protection of the 3-hydroxyl group is carried out by the reaction with chloromethyl methyl ether or chloromethyl ethyl ether in a solvent such as dimethylformamide, dimethylsulfoxide (DMSO), hexamethylphosphoramide, and tetrahydrofuran which may be used alone or in combination, in the presence of an inorganic base such as potassium carbonate, sodium carbonate, and sodium hydroxide, at a temperature ranging from $0°$ to $40°$ C. (desirably at about $25°$ C.), and the reaction is completed in 1 to 18 hours.

In this way the compound (II) wherein the hydroxyl groups at the 3-, 5-, and 6-positions have been protected, can be obtained.

The compound (III) can be produced by the reaction of the alcohol derivative of the aliphatic hydrocarbon or alicyclic hydrocarbon groups represented by R with a phosphorylating agent such as phosphoric acid monoester dihalogenide.

Solvents used in the phosphorylation include aromatic hydrocarbons (e.g. benzene, toluene), ethers (e.g. diethyl ether, diisopropyl ether, dioxane, tetrahydrofuran), esters (e.g. ethyl acetate), halogenated hydrocarbons (e.g. methylene chloride, chloroform); dimethylformamide, and the mixtures thereof, the reaction temperature ranges from about $-10°$ to $50°$ C., and the reaction time ranges from 1 to 10 hours.

The compounds (I) and the salts thereof in this invention prevent and improve the dysfunction caused by oxygen free group in an ischemia-reperfusion model of the rat heart, and the toxicity is very weak. Therefore the compounds (I) and the salts thereof can be used as therapeutic, preventive and improving agents against various dysfunction in the circulatory system in mammals (e.g. mouse, rat, rabbit, dog, monkey, human), such as ischemic heart disorders (arrhythmia, coronary spasm, necrosis of heart tissue, myocardial infarction, etc.), disorders due to subarachnoid hemorrhage, disorders due to ischemic cerebral tissue (e.g. cerebral infarction, dementia, senile dementia), ischemic renal disorders, ischemic hepatic disorders, and ischemic disorders in the digestive system (e.g. ulcers in the digestive tract).

The concrete examples of the use of the compounds for prevention, treatment and improvement of the disorders of the circulatory system are anti-arrhythmic agents, antimyocardial infarction agents, anti-cerebral infarction agents, agents for prevention of dementia and senile dementia, various circulatory disorders-improving agents such as those for treatment and improvement after subarachnoid hemorrhage and those for improvement of the prognosis of organ transplantation, renal function-improving agents, and therapeutic agents for stress ulcers in digestive organs.

The compounds (I) of this invention have low toxicity, and therefore the compounds (I) and the salts thereof can safely be administered orally or parenterally in the form of pharmaceutical composites [e.g. tablets, capsules (including soft capsules and microcapsules), liquid preparations, suppositories, injections, transnasal preparations] prepared according to the per se known methods by mixing with pharmaceutically acceptable carriers, excipients, and diluents.

The dosing level is dependent on the subjects to be administered, route of administration, symptoms, etc., but the usual unit dose for oral administration in mammals described above ranges from about 0.1 mg/kg to 50 mg/kg body weight, preferably about 0.5 mg/kg to 20 mg/kg body weight which is given once to three times a day.

For parenteral administration, for example as a suppository, about 5 mg/kg to 10 mg/kg on the compound (I) basis is enough when given once or twice a day. As an injection, about 0.1 mg/kg to 5 mg/kg on the compound (I) basis is desirably given once or twice a day.

In the course of production of the oral preparations (e.g. tablets) described above, binders (e.g. hydroxypropylcellulose, hydroxymethylpropylmethylcellulose, macrogaol), disintegrators (e.g. starch, calcium carboxymethylcellulose), excipients (e.g. lactose, starch), lubricants (e.g. magnesium stearate, talc), etc. may be combined appropriately.

In the course of production of the parenteral preparations (e.g. injections), isotonicity providing agents (e.g. glucose, D-sorbitol, D-mannitol, sodium chloride), antiseptics (e.g. benzylalcohol, chlorobutanol, methyl p-hydroxybenzoate, propyl p-hydroxybenzoate), or buffering agents (e.g. phosphate buffer, sodium acetate buffer) may be combined appropriately.

EXAMPLES

The following experimental examples and examples will explain this invention in more detail.

EXPERIMENTAL EXAMPLE 1

Suppression of production of peroxidized lipids in rat brain homogenate:

(i) Method

Male SD rats (10 to 12-week-old) were subjected to venesection under anesthesia with pentobarbitol, and the brain tissues were excised, the brain tissues were homogenized in phosphate buffer (pH 7.4) to make a 5% homogenate. The said homogenate was incubated at 37° C. for one hour, and the amount of peroxidized lipids produced was determined according to the thiobarbituric acid (TBA) method as described by Ohkawa et al. [Analytical Biochemistry, 95, 351 (1979)]. The test drug was added to the 5% homogenate before incubation so that the final concentration became $10^{-4}$ M. The suppression of production of peroxidized lipids is expressed in % suppression relative to the production in the group given only the solvent (DMSO).

(ii) The result is shown in Table 1.

As shown in Table 1, the compound (I) of this invention suppressed the production of peroxidized lipids. The 2-phosphoric acid ester of ascorbic acid used as the control did not show the suppressing effect.

| Compound | No. of animals used (n) | Rate of suppression (%) |
|---|---|---|
| 1 | 4 | 43.7 ± 5.1 |
| 18 | 3 | 75.8 ± 10.8 |
| AP | 2 | −12.5 |

EXPERIMENTAL EXAMPLE 2

Experiment on reduction of foci of myocardial infarction due to coronary obstruction-reperfusion in rat:

(i) Method

Male Wistar rats (weighing 276 to 330 g each) were subjected to median thoracotomy under anesthesia with pentobartitol, and the left anterior descending coronary arterial branch (LAD) was kept obstructed at the origin for one hour, and then reperfused. After 30 to 60 minutes of reperfusion the thorax was closed and the animals were kept conscious. After 24 hours the heart was again excised under anesthesia, and the left ventricle was sliced. The slices were stained with triphenyltetrazolium chloride (TTC) at 37° C. for 15 minutes and the infarcted foci were weighed.

The test drug was dissolved in physiological saline and given from the femoral vein at the dose of 5 mg/kg 30 minutes after obstruction of LAD. To the control group only physiological saline was given.

(ii) Results

The results are summarized in Table 2. The compound of this invention reduced the foci of myocardial infarction by 55%, but AP did not.

TABLE 2

| Compound | No. of animals | (n) Foci of myocardial infarction (% of left ventricle weight) | Rate of suppression (%) |
|---|---|---|---|
| Control | (8) | 35.0 ± 2.9* | |
| 1 | (4) | 16.4 ± 4.3 | −55 |
| AP | (4) | 34.1 ± 4.4 | — |

*The figures are means ± SEM.
AP: 2-phosphoric acid ester of ascorbic acid

EXAMPLE 1 disodium 2-O-(octadecyloxyphosphoryl)ascorbate (Compound 1)

Octadecyl alcohol (5.4 g) was dissolved in the mixture of toluene (40 ml) and pyridine (8 ml), and the resultant solution was added dropwise to the solution of phosphorus oxychloride (6 g) in toluene (60 ml) with ice-cooling. The reaction mixture was stirred at room temperature for 3 hours, the deposited crystals were removed by filtration, and the filtrate was concentrated under reduced pressure. The residue was dissolved with ice-cooling to the solution was added dropwise by ice-cooling to the solution of 5,6-0-isopropylideneascorbic acid (5.2 g) in a mixture of tetrahydrofuran (100 ml) and pyridine (4 ml). After stirring for 1 hour, the reaction mixture was concentrated under reduced pressure, the residue was dissolved in ethanol (50 ml), to which 1N hydrochloric acid (50 ml) was added, and the mixture was stirred at 50° C. for 20 minutes by heating. After cooling the mixture was concentrated under reduced pressure, the residue was dissolved in ethyl acetate, washed with water, dried ($MgSO_4$), and concentrated under reduced pressure. The resultant crude crystals were recrystallized from isopropyl ether/ethyl acetate, to give 2-O-(octadecyloxyphosphoryl) ascorbic acid (5 g). This product was dissolved in ethanol (50 ml), to which sodium methylate (28% solution in methanol) was added dropwise, and the deposited crystals were collected by filtration, to give the desired compound (5.1 g) as white powders.

m.p.: >220° C. (decomp.).

Elemental analysis for $C_{24}H_{43}O_9Na_2P$

Calcd. (%): C, 52.17; H, 7.84

Found (%): C, 51.92; H, 8.01.

IR spectrum (Kbr) $cm^{-1}$: 2910, 1733, 1596.

NMR spectrum: internal standard; sodium 3-(trimethylsilyl)propanesulfonate) ($D_2O$):δ: 4.46 (1H, s), 3.90 (3H, m), 3.72 (2H, m), 1.61 (2H, m), 1.27 (30H, s), 0.88 (3H, m).

EXAMPLE 2:

disodium 2-O-(5,6-dimethoxy-3-methyl-1,4-benzoquinon-2-yl)decyloxyphosphoryl)ascorbate (Compound 2)

6-(10-Hydroxydecyl)-2,3-dimethoxy-5-methyl-1,4-benzoquinone (1.0 g) was dissolved in the mixture of toluene (7 ml) and pyridine (1.5 ml), and the resultant solution was added dropwise to the solution of phosphorus oxychloride (0.92 g) in toluene (10 ml) by ice-cooling. The reaction mixture was stirred at room temperature for 3 hours, the deposited crystals were removed by filtration, and the filtrate was concentrated under reduced pressure. The residue was dissolved in toluene (7 ml), and the solution was added dropwise with ice-cooling to the solution of 5,6-O-isopropylidine-3-ethoxymethylascorbic acid (0.86 g) in the mixture of tetrahydrofuran (20 ml) and pyridine (0.6 ml). After stirring for 1.5 hour, the reaction mixture was concentrated under reduced pressure, the residue was dissolved in ethanol (10 ml), to which 1N hydrochloric acid (10 ml) was added, and the mixture was stirred at 50° C. for 20 minutes by heating. After cooling the mixture was concentrated under reduced pressure, the residue was dissolved in ethyl acetate, washed with saline, dried with anhydrous magnesium sulfate, and concentrated under reduced pressure. The residue was dissolved in ethanol (20 ml), to which a solution of sodium hydroxide in ethanol was added dropwise, and the deposited crystals were collected by filtration and dissolved in water (20 ml). The insoluble matter was removed by filtration, the filtrate was brought to pH 2 with 1N hydrochloric acid, extracted with ethyl acetate, washed with saline, dried with anhydrous magnesium sulfate, and concentrated under reduced pressure. The residue was dissolved again in ethanol (20 ml), to which a solution of sodium hydroxide in ethanol was added dropwise with stirring to make pH 5. The deposited crystals were collected by filtration, to give powdery crystals (70 mg).

m.p.: 185° C. (decomp.).

NMR spectrum (δ): 1.28 (16H, m), 1.61 (2H, m), 1.99 (3H, s), 2.44 (2H, m), 3.73 (2H, m), 3.95 (6H, s), 3.99 (3H, m), 4.48 (1H, brs).

EXAMPLE 3 disodium 2-O-(ethylphosphoryl)-6-O-stearoylascorbate (Compound 3)

Ethyl dichlorophosphate (0.81 g) was dissolved in toluene (20 ml), and the resultant solution was added dropwise to the solution of 6-O-stearoylascorbic acid (2.65 g) in a mixture of tetrahydrofuran (60 ml) and pyridine (2 ml) by ice-cooling. After stirring for 1.5 hours, 1N hydrochloric acid (10 ml) was added. The mixture was extracted with ethyl acetate, washed with water, dried with anhydrous magnesium sulfate, and concentrated under reduced pressure. The residue was dissolved in ethanol (30 ml), to which a solution of sodium hydroxide in methanol was added dropwise, and the deposited crystals were collected by filtration, to give powdery crystals (2.1 g).

m.p.: >165° C. (decomp.).

NMR spectrum (δ): 0.88 (3H, m), 1.25 (31H, m), 1.61 (2H, m), 2.41 (2H, s), 4.00 (2H, m), 4.24 (3H, m), 4.51 (1H, brs).

EXAMPLE 4

The compounds listed in Table 3 were produced similarly as described in Examples 1 to 3.

TABLE 3

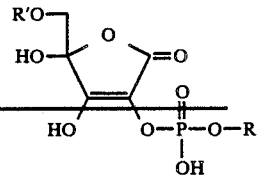

| Compd. No. (Method Ex. No.) | $R^1$ R | Molecular formula Temp. of Dec. (°C.) | Elemental Anal. (CH) (Cald.) Found | NMR (δ, ppm, $D_2O$) |
|---|---|---|---|---|
| 4 (1) | H $C_2H_5$ | $C_8H_{11}O_9PNa_2.0.5H_2O$ >220 | (28.50 3.59) 28.40 3.87 | 1.28(3H, t, J=7Hz), 3.74(2H, m), 4.04(3H, m), 4.50(1H, brs). |
| 5 (1) | H $CH_3(CH_2)_{11}$ | $C_{18}H_{32}O_9PNa.H_2O$ >180 | (46.55 7.37) 46.73 7.80 | 0.88(3H, m), 1.31(16H, m), 1.65 (2H, m), 3.73(2H, m), 4.00(3H, m) |
| 6 (1) | H $CH_3(CH_2)_{15}$ | $C_{21}H_{37}O_9PNa_2.2H_2O$ >180 | (47.14 7.73) 47.14 7.81 | 0.88(3H, m), 1.29(24H, m), 1.65(2H, m), 3.72(2H, m), 4.02(3H, m), 4.50(1H, brs). |
| 7 (1) | H $CH_3(CH_2)_{19}$ | $C_{26}H_{48}O_9PNa.H_2O$ >190 | (54.16 8.74) 54.24 8.83 | 0.88(3H, m), 1.26(34H, m), 1.65(2H, m), 3.74(2H, m), 4.02(3H, m), 4.47(1H, brs). |
| 8 (1) | H $CH_3(CH_2)_{19}$ | $C_{26}H_{49}O_9P$ mp. 76–77 (AcOEt-iPr$_2$O) | | ($d_6$-DMSO): 0.85(3H, m), 1.22(34H, m), 1.50(2H, m), 3.42(2H, m), 3.71(1H, m), 3.80(2H, m), 4.73(1H, brs). |
| 9 (1) | H Oleyl (C 18:1) | $C_{24}H_{45}O_9PNa_2$ >190 | (51.98 8.18) 52.31 7.87 | 0.87(3H, m), 1.25(22H, m), 1.64 (2H, m), 1.99(4H, m), 3.74(2H, m), 4.02(3H, m), 4.45(1H, brs), 5.35 (2H, m). |
| 10 (1) | H Erucyl (C 22:1) | $C_{28}H_{50}O_9PNa.H_2O$ >185 | (55.80 8.70) 55.50 8.88 | 0.87(3H, m), 1.26(32H, m), 1.65 (2H, m), 2.00(4H, m), 3.74(2H, m), 4.02(3H, m), 4.45(1H, brs), 5.32 (2H, m). |
| 11 (1) | H Linoleyl (C 18:2) | $C_{24}H_{39}O_9PNa_2.1.2H_2O$ >180 | (50.56 7.32) 50.58 7.62 | 0.87(3H, m), 1.31(16H, m), 1.62 (2H, m), 2.03(4H, m), 2.76(2H, m), 3.74(2H, m), 4.01(3H, m), 4.47 (1H, brs), 5.37(4H, m). |
| 12 (3) | $CH_3(CH_2)_{16}CO$ $C_2H_5$ | $C_{26}H_{45}O_{10}PNa_2.0.5H_2O$ >165 | (51.73 7.68) 52.18 8.14 | 0.88(3H, m), 1.26(31H, m), 1.61 (2H, m), 2.41(2H, m), 4.00(2H, m), 4.24(3H, m), 4.51(1H, brs). |
| 13 (1) | H $Ph(CH_2)_3$ | $C_{15}H_{17}O_9PNa_2.2H_2O$ >170 | (39.66 4.66) 39.27 4.26 | 1.93(2H, m), 2.72(2H, t, J=7.5 Hz), 3.73(2H, m), 4.00(3H, m), 4.48(1H, brs), 7.32(5H, m). |
| 14 (1) | H β-Cholestan-3-yl | $C_{33}H_{53}O_9PNa_2.2H_2O$ >220 | (56.08 8.13) 55.81 7.93 | 0.5–2.1(46H, m), 3.74(2H, m), 4.07(2H, m), 4.48(1H, brs). |
| 15 (1) | H (S)-(−)-β-Citronelyl | $C_{18}H_{25}O_9PNa.2H_2O$ >150 | (42.48 6.68) 42.68 6.37 | 0.88(3H, d, J=6Hz), 1.1–1.8 (5H, m), 1.60(3H, s), 1.67(3H, s) 2.00(2H, m), 3.73(2H, m), 4.04 (3H, m), 4.56(1H, brs), 5.23 (1H, m) |
| 16 (1) | H $CH_3(CH_2)_{16}$ | $C_{23}H_{41}O_9PNa_2$ >180 | (50.45 7.73) 50.11 8.06 | 0.88(3H, m), 1.29(26H, m), 1.65 (2H, m), 3.72(2H, m), 4.02(3H, m) 4.47(1H, brs). |
| 17 (1) | H Tol$_2$C=CH—(CH$_2$)$_5$ | $C_{27}H_{31}O_9PNa_2$ >215 | | 1.20(6H, m), 1.95(2H, m), 2.00 (3H, s), 2.15(3H, s), 3.66(2H, m) 3.95(3H, m), 4.41(1H, brs), 5.91(1H, m), 6.85(8H, m). |
| 18 (1) | H $CH_3(CH_2)_{21}$ | $C_{28}H_{51}O_9PNa_2$ >220 | (55.25 8.45) 55.23 8.62 | 0.87(3H, m), 1.27(38H, m), 1.52 (2H, m), 3.69(2H, m), 4.00(3H, m) 4.42(1H, m). |

Tol: p-methylphenyl
Ph: phenyl

What is claimed is:
1. A compound represented by the formula:

wherein $R^1$ is a hydrogen atom, carboxylic acid acyl or carbamoyl which may be substituted with $C_{1-3}$ alkyl, $C_{1-3}$ alkoxy, methylenedioxy or halogen; and R is
(1) an aliphatic hydrocarbon group which may be substituted with hydroxy which may be substituted with $C_{1-20}$ alkyl, phenyl which may be substituted with halogen, $C_{1-3}$ alkoxy or $C_{1-3}$ alkyl, quinonyl which may be substituted with $C_{1-3}$ alkoxy or $C_{1-3}$ alkyl, or chroman-2-yl which may be substituted with $C_{1-3}$ alkyl, $C_{1-3}$ alkoxy, hydroxy or phenyl, or (2) an alicyclic hydrocarbon group which may be substituted with $C_{1-3}$ alkoxy, $C_{1-3}$ alkoxycarbonyl, hydroxy, halogen, $C_{1-10}$ alkyl, $C_{2-10}$ alkenyl or $C_{2-10}$ alkynyl, or a pharmaceutically acceptable salt thereof.

2. The compound according to claim 1, wherein the aliphatic hydrocarbon group is a straight-chain alkyl.

3. The compound according to claim 2, wherein the straight-chain alkyl is unsubstituted and has 1 to 30 carbon atoms.

4. The compound according to claim 1, wherein the aliphatic carbon group is a straight-chain alkenyl which may be substituted.

5. The compound according to claim 4, wherein the straight chain alkenyl is unsubstituted and has 5 to 24 carbon atoms with 1 to 4 double bonds.

6. The compound according to claim 1, wherein the alicyclic hydrocarbon residue is a monocyclic hydrocarbon group or condensed polycyclic hydrocarbon group which may be substituted with $C_{1-3}$-alkyl or hydroxy.

7. The compound according to claim 1, wherein the carboxylic acid acyl is a $C_{1-22}$ fatty acid acyl or benzoic acid acyl, which may be substituted with $C_{1-3}$-alkyl.

8. The compound according to claim 1, wherein $R^1$ is a hydrogen atom and R is a straight-chain alkyl of 9 to 22 carbon atoms.

9. The compound according to claim 1, which is disodium 2-O-(octadecylphosphoryl)ascorbate.

10. The compound according to claim 1, which is disodium 2-O-(linoleylphosphoryl)ascorbate.

11. An anti-ischemic pharmaceutical composition which contains an anti-ischemic effective amount of a compound according to claim 1 and a pharmaceutically acceptable carrier, excipient or diluent therefor.

12. A method of preventing or treating a dysfunction in the circulatory system in a mammal which comprises administering to the mammal an effective anti-ischemic amount of the compound according to claim 1.

* * * * *